United States Patent [19]

Langen et al.

[11] Patent Number: 5,357,427
[45] Date of Patent: Oct. 18, 1994

[54] REMOTE MONITORING OF HIGH-RISK PATIENTS USING ARTIFICIAL INTELLIGENCE

[75] Inventors: Pauline A. Langen, Simsbury; Jeffrey S. Katz, West Hartford, both of Conn.; Gayle Dempsey, Needham, Mass.; James Pompano, East Haven, Conn.

[73] Assignee: Digital Equipment Corporation, Maynard, Mass.

[21] Appl. No.: 31,752

[22] Filed: Mar. 15, 1993

[51] Int. Cl.$^5$ ............................................. G06F 15/42
[52] U.S. Cl. ............................................. 364/413.02
[58] Field of Search ............... 364/413.01, 413.02, 364/274, 274.1, 274.3, 274.8, 275.7, 413.03; 395/1, 2, 924

[56] References Cited

U.S. PATENT DOCUMENTS

| | | | |
|---|---|---|---|
| 4,254,304 | 3/1981 | Fulghum et al. | 179/2 |
| 4,426,555 | 1/1984 | Underkoffler | 179/84 |
| 4,803,625 | 2/1989 | Fu et al. | 364/413.03 |
| 4,894,787 | 1/1990 | Flannelly et al. | 364/508 |
| 4,962,473 | 10/1990 | Crain | 364/900 |
| 5,056,513 | 10/1991 | Boutin | 128/204.23 |
| 5,058,113 | 10/1991 | Burnham et al. | 371/15.1 |
| 5,123,017 | 6/1992 | Simpkins et al. | 371/15.1 |

OTHER PUBLICATIONS

Group Health Institute "Proceedings" Jun. 8, 1992, Benefits of Integrating Voice Technology and Artificial Intelligence to Home Health Monitoring Services, by Pauline Langen.

*Primary Examiner*—Donald E. McElheny, Jr.
*Attorney, Agent, or Firm*—Rama B. Nath; Ronald C. Hudgens; Albert P. Cefalo

[57] ABSTRACT

Method and system for remote monitoring of high-risk patients using artificial intelligence. A plurality of high-risk patients can be simultaneously monitored without patient intervention. A patient hears questions in the doctor's voice at each monitoring encounter and responds. The patient's responses are recorded at a remote central monitoring station and can be analyzed on line or later. Artificial intelligence (AI) and voice technology (DECvoice) are combined to present to the patient, during a monitoring session or encounter, questions which would be selected from a plurality of different recorded questions. Questions to the patient are chosen using AI, based on the patient's response, by parsing. The monitor could take several forms such as for e.g., uterine activity strips, glucometers, blood pressure cuffs, pulse monitors, electroencephalographs, etc. Preferably, four telephone lines are dedicated to each patient, one for the monitor, one for the voice, one as a back up and one to sense failures. Dual tone matrix frequency signals (DTMF) may be used for transmission of monitored signals and other information which can be recognized by DECvoice, which is but one example of the voice technology which can be used.

12 Claims, 7 Drawing Sheets

FIG. 1
HOME HEALTH MONITORING USING
TRANS-TELEPHONIC MEDICINE

FIG. 2
CONNECTIVITY

| GEORGE-BUSH, A DEPRESSED-PATIENT ||
|---:|:---|
| NOTES | OK |
| USER RESTRICTIONS | NONE |
| NAMES | GEORGE-BUSH |
| AGE | 67 |
| SEX | MALE |
| CLINICIAN | C. EVERETT.KOOP |
| DIAGNOSIS | DELUSION-WITH-NAUSEA |
| SESSIONS | **** |
| MEDICATION REGIME | TIGAN |
| TROUBLE SLEEPING | **** |
| WAKING EARLY | 1 |
| WAKING DURING NITE | **** |
| TROUBLE WITH APPETITE | **** |
| SLOWED DOWN | **** |
| NERVOUS AGITATED | **** |
| IRRITABLE TENSE | **** |
| TROUBLE CONCENTRATING | 1 |
| LITTLE PLEASURE | **** |

FIG. 5

| MIKAEL. AN ANXIOUS-PATIENT | |
|---|---|
| NOTES | OK |
| USER RESTRICTIONS | NONE |
| NAMES | MIKAEL |
| PATIENT NAME | MIKAEL.J. GORBACHEV |
| PATIENT AGE | 70 |
| PRESCRIBED MEDS | TYLENOL-EXTRA-STRENGTH |
| ZUNG RATING | NONE |
| BREATHALYZER READING | NONE |
| DIAGNOSIS | PROCRASTINATOR |
| PT CLINICIAN | DR. ZHIVAGO |
| LAST DIALOGUE DATE | NONE |
| LAST VISIT DATE | NONE |
| PRESENT CONCLUSIONS | NONE |
| ANALYSIS STATUS | **** |

FIG. 6

GREETING

HELLO,[DP-NAME],THIS IS [DP-CLINICIAN]CALLING. I'D LIKE TO ASK YOU A FEW QUESTIONS,IF YOU HAVE TIME. IS THIS A CONVENIENT TIME FOR YOU?

HIDE

⦿ CONVENIENT TIME

◯ INCONVENIENT TIME

FIG. 7

ACCOMPANYING SYMPTOM

[HIDE]

WE WOULD LIKE NOW TO MONITOR SOME OF THE OTHER SYMPTOMS THAT MAY ACCOMPANY DEPRESSION. ARE YOU STILL EXPERIENCING..

- [?] WAKING EARLY IN A.M.
- [X] TROUBLE FALLING-ASLEEP
- [?] WAKING DURING THE NIG
- [?] TROUBLE WITH YOUR APP
- [X] FEELING SLOWED DOWN
- [?] NERVOUS OR AGITATED
- [?] MORE IRRITABLE, TENSE
- [?] TROUBLE CONCENTRATING
- [?] LITTLE OR NO PLEASURE

FIG. 8

NEW-PROBLEMS

[HIDE]

HAVE ANY NEW PROBLEMS COME ABOUT THAT HAS CONTRIBUTED TO YOUR FEELING BADLY? DO YOUR NEW PROBLEMS HAVE TO DO WITH ...

- [?] FAMILY
- [X] WORK
- [?] MEDICAL PROBLEMS
- [?] PHYSICAL PROBLEMS
- [X] FINANCIAL PROBLEMS
- [?] PRESCRIBED MEDICINE
- [X] MEMORY
- [X] SPECIFIC THOUGHTS
- [?] MOOD

FIG. 9

| MED-REMINDER | HIDE |

AS A MEDICATION REMINDER, YOU SHOULD REMEMBER [DP], THAT ON [DP-DATE] YOU WERE GIVEN A PRESCRIPTION FOR DESIPRAMINE, 50 mg.[OR DP-RX] TABLETS, AND YOU WERE GIVEN A TOTAL OF 100 TABLETS. THIS SHOULD BE ENOUGH TO LAST UNTIL [DP-DATE+100] IF YOU ARE TAKING THE MEDICINE AS PRESCRIBED. PLEASE BE SURE THAT YOU DO NOT RUN OUT OF THE MEDICINE ACCIDENTLY.

FIG. 10

WHY-NOT-MEDS-RULES

FOR ANY DEPRESSED-PATIENTS DP WHENEVER THE SIDE-EFFECTS-Q SEQ OF DP RECEIVES A VALUE AND WHEN SEQ IS TRUE THEN INFORM THE OPERATOR THAT "THE PATIENT [THE NAME OF DP] HAS SIDE EFFECTS FROM THE MEDICINE"

FOR ANY DEPRESSED-PATIENTS DP WHENEVER THE NO-LONGER-NEED-Q NING OF DP RECEIVES A VALUE AND WHEN NING IS TRUE THEN INFORM THE OPERATOR THAT "THE PATIENT[ THE NAME OF DP] NO LONGER NEEDS THIS MEDICINE"

FOR ANY DEPRESSED-PATIENTS DP WHENEVER THE FORGET-Q FQ OF DP RECEIVES A VALUE AND WHEN FQ IS TRUE THEN INFORM THE OPERATOR THAT "THE PATIENT [ THE NAME OF DP] FORGETS TO TAKE HIS MEDICINE"

FIG. 11

REMOTE MONITORING OF HIGH-RISK PATIENTS USING ARTIFICIAL INTELLIGENCE

FIELD OF THE INVENTION

This invention relates generally to simultaneous remote monitoring of a plurality of high risk patients by a healthcare practitioner; more particularly, the invention concerns simultaneous remote monitoring of a plurality of high risk patients without patient intervention and using artificial intelligence (AI).

BACKGROUND OF THE INVENTION

Continual patient monitoring in certain types of patient condition becomes a necessity to assure timely intervention by a healthcare practitioner or a physician to initiate the right medical procedure or administer the required medication in a timely manner. Situations with high-risk patients in the areas of cardiology, obstetrics, neurology, psychology are but some examples where continual remote patient monitoring becomes a patient care necessity.

With increasing hospitalization costs for patients, health insurance companies and health maintenance organizations are encouraging more and more patients to reduce the duration of hospitalization if hospitalization is an absolute necessity. In the face of increasing healthcare costs, certain kinds of treatment, including chemotherapy, antibiotic therapy, infusion therapy and pneumonia treatment are all considered relatively safe, cost effective home treatments. Several infusion devices have been approved by the FDA with the proviso that such devices be calibrated at regular intervals as prescribed. There are other situations such as in the field of obstetrics wherein patients are encouraged to wait as long as medically desirable before patients enter a hospital for childbirth. Typically, in the obstetrics patient situation, a patient, by home monitoring of the frequency and duration of uterine contractions can determine if it is time to enter a hospital or any other facility for childbirth. Such determination however needs patient participation or intervention. There may be situations however, where patient participation is not possible or patient intervention is not to be relied upon, but patient monitoring is nevertheless necessary. Another example of such a situation is a cardiac patient. A reliable but expensive method of monitoring in such situations is for a nurse or healthcare worker or a physician to meet the patient in person to do the monitoring. Notwithstanding, if continual monitoring is necessary, it will then necessitate the nurse or healthcare worker or physician to be physically present at the patient site during the monitoring. This will limit the number and type of patients that can be covered in a given time by a healthcare worker.

Some solutions to the above problem are offered by patient care monitoring services which sometimes are offered by health maintenance organizations (HMO). Statistics indicate that corporate healthcare benefits represented about 5% of the payroll in 1980 as compared with 14% in 1990. Part of the corporate healthcare benefits are patient monitoring costs, and reducing such costs will be a very attractive proposition. In any event it is important to note that avoidance of clinically unnecessary outpatient visits can be a key to reducing healthcare costs, if insurance liability can be reduced and the clinical integrity preserved.

It is known in prior art to generate signals representing a patient's condition and record them for later scrutiny by a physician. An example of such is the well known Holter heart monitor, wherein a continuous 24 hour cardiogram of a patient is recorded by a monitor which is worn by the patient. Functionally however, in such a monitoring system a healthcare worker or a physician is not alerted by any emergency situation which could occur during the duration of the monitoring.

The underlying considerations in providing improved health monitoring services for high risk patients include the facts that:

(i) a high risk patient likes to hear the doctor's voice during the monitoring interaction;
(ii) the doctor has the responsibility to determine in a timely manner as to whether an appointment is necessary,
(iii) the doctor should have the opportunity of determining if the high risk patient is in need of any urgent medication or any change in the treatment,
(iv) it is often undesirable for monitoring to be done by patient intervention especially in situations like acute hypertension cases or serious perinatal cases.
(v) it is desirable to minimize the continuous use of a nurse or other healthcare worker to personally attend to the patient and do the monitoring,
(vi) it would be undesirable and disadvantageous to use acoustic telephone devices like modems which would be ineffective and uneconomical to use for remote monitoring purposes, and
(vii) it is desirable if a physician/doctor could attend simultaneously and remotely to a large number of high risk patients so that doctor intervention or other remedial measure could be initiated when necessary and no sooner.

Previous approaches by others to address this problem in general, as aforesaid, have been to use an intermediary, (a visiting nurse, or similar representative) to call on the patient, and take the physical data (temperature, pulse, blood pressure, fetal heart monitor, glucose level, etc. ), and report those results to the clinicians' office by mail or telephone. This means that only the recorded physical data is being obtained. The physical data must still be viewed by the doctor to evaluate his patient. And, again, another level of human intervention to monitor the patient is required for each patient. Health software services, such as Healthdyne, ® Inc. use a nurse to transmit the data from the patient, and then their software evaluates the patient's medical condition. Both of these methods are costly because of the human intervention of a healthcare worker or a nurse visiting each patient.

This is not the same as a doctor himself, speaking to each of his high-risk patients, evaluating their need for attention, and obtaining the data from the monitoring devices on those patients simultaneously.

There is need for an improved patient monitoring system including method and apparatus, which is both patient friendly and doctor friendly and increases the patient care quality without increasing clinically unnecessary patient visits. There is also need for such a system to be accurate and reliable, to use normal telephone lines, to be easy for maintenance, future upgrading, additions and changes.

The present invention provides a health monitoring system including method and apparatus for monitoring, without patient intervention and using artificial intelligence, the medical condition of a remotely located patient by means of monitor-generated signals through telephone lines reaching an interface to the medical expert system application. Voice technology and AI are integrated in the innovative system offering significant economic benefits in the home healthcare industry. As described hereinafter, the AI used in the innovative health monitoring system is governed by physician-provided guidelines, standards and approach. Advantageously, the patient is presented questions in the physician's own voice, and the questions and their pattern would be chosen from prerecorded conversation of the physician which would be parsed and presented to the patient depending on the patient's response to each question and as guided by AI.

A clear benefit is perceived by the patients using the inventive monitoring system in that they view the physician "conversation" as providing an increased level of physician contact, concern and care. Such a patient perception becomes a significant marketing tool for the inventive system in the healthcare industry. The innovative monitoring system described hereinafter provides for simultaneous multiple monitoring of several high risk patients who might have different types of ailments. The system described and claimed herein allows a medical practitioner, hospital, or group health provider to expand their service market, without risk of losing quality of service. In fact, it is the consistent application of the physician-provided rules of monitoring patient parameters that allows the system to advise the doctor routinely about his patients. He can be more productive because he is directed to critical patient needs, while unnecessary outpatient visits are reduced. Moreover, the fact that the multiple physician-patient "conversations" are initiated by the system, and can be carried on simultaneously, means that the physician is increasing his services without increasing his time to converse with patients.

Because of the AI/Voice technology combination, appropriate clinical questions are asked, (through "reasoning" about a response, and branching to another relevant question, or portion of a question)—by a physician, forward and backward chaining in Artificial Intelligence. In addition, the AI/Voice technology allows it to simultaneously carry on multiple (approximately 48) conversations, monitoring the results, and to include features such as call monitoring, call forwarding, and call recording whenever physician-directed rules indicate that intervention and alarming are needed. Thus, if an HMO were providing high-risk pregnancy patients with home health monitoring, the obstetrician would be notified immediately of an out-of-limits fetal heart rate on a patient. The system would detect the change, notify the HMO monitoring assistant by opening a window on their computer screen, merging recent medical data on the patient, and also forwarding the call to the HMO monitoring assistant. It is to be noted that in all of its functionality, the AI/Voice/Monitoring is not intended to diagnose; rather it advises the clinician of possible need to intervene.

Physicians who would use the inventive monitoring system would easily view the system as a superior clinical tool, since it frees them from being tied to one high risk patient at a time and also since they are not relying upon a patient to read a monitoring device. The system allows a physician user to be warned of critically-ill patients automatically according to the physician's own chosen guidelines as controlled by the AI.

In a preferred embodiment described hereinafter a DECvoice 1-168 VAX System is used which offers the capability of simultaneously monitoring 48 remote patients all connected in to a central monitoring and recording system, such as for e.g., a computer integrated telephone system.

BRIEF DESCRIPTION OF THE DRAWING

A more detailed understanding of the invention may be had from the following description of a preferred embodiment, given by way of example and to be understood in conjunction with the accompanying drawing wherein.

DESCRIPTION OF THE PREFERRED EMBODIMENT

Figure 1:
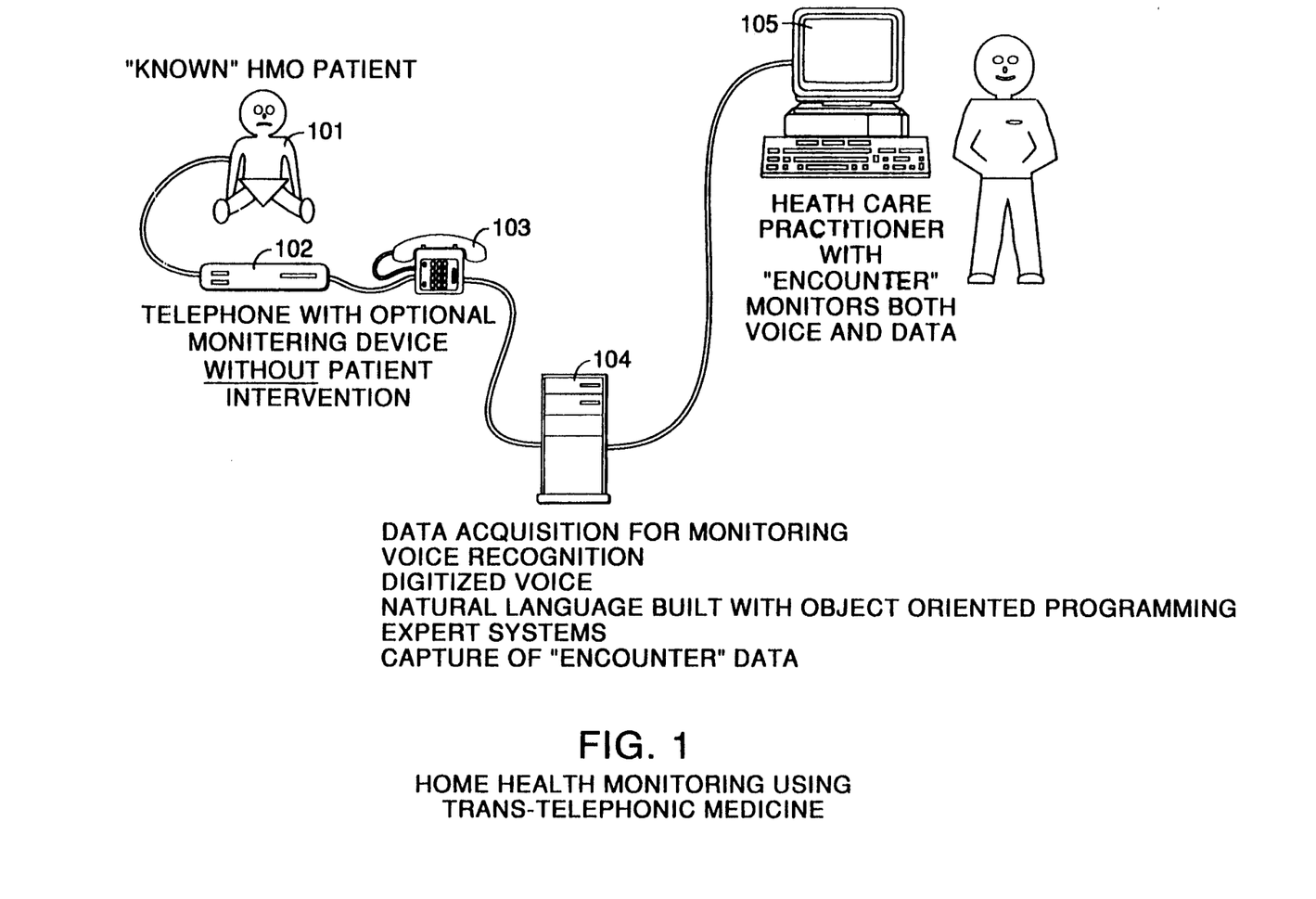
FIG. 1 illustrates a pictorial representation of a remote monitoring system using (AI) Expert Systems wherein each new monitoring contact initiated by the healthcare practitioner with a known HMO patient is termed an "Encounter"

As illustrated, FIG. 1 shows a known HMO patient 101 whose condition will be monitored by the monitoring device, which, as aforesaid could take any form such as for example, blood pressure cuff, pulse monitor, uterine activity strips, glucometer or electroencephalograph (EEG) etc. If an infant is being remotely monitored, the illustrated embodiment will need to be modified to the extent that a "conversation" with the patient may not be practical, but the system would still function to enable and ensure timely intervention by a healthcare person or a physician.

As developed, an AI program directs the physician-patient conversation through voice technology, measuring physical parameters near the end of the conversation. The physician previously would have recorded questions typically asked during a patient examination; the AI program parses the questions and selects specific follow-up questions, depending upon the patient's responses. The automatic monitoring (note, the patient is not required to read the device) may take place at the end of the phone conversation, where the AI system commands the voice system to play the physician-recorded request to place the monitor in position, and the recording function takes place. The patient monitoring device might use AT&T's Dual-Tone Matrix Frequency (DTMF) standard for touch-tone telephones, which DECvoice hardware (the Voice Synthesis/Recognition technology) can recognize. An inexpensive (less than $50.00) encoding device is used to translate the analog signal coming from the home monitoring instruments to the telephone. See FIG. 1.

The Artificial Intelligence system is driven by a simple to use Natural Language interface which directs the Voice system to send ("speak") appropriate questions, recognize ("listen for") the patient's answers, update the patient's database, direct the telephone-patient monitoring, and advises the HMO facility of critical patient conditions. The information acquired from the patient calls is available to the medical practitioner on both a real-time basis when the calls are being made, or on an ad-hoc basis after the calls are logged.

Figure 2:
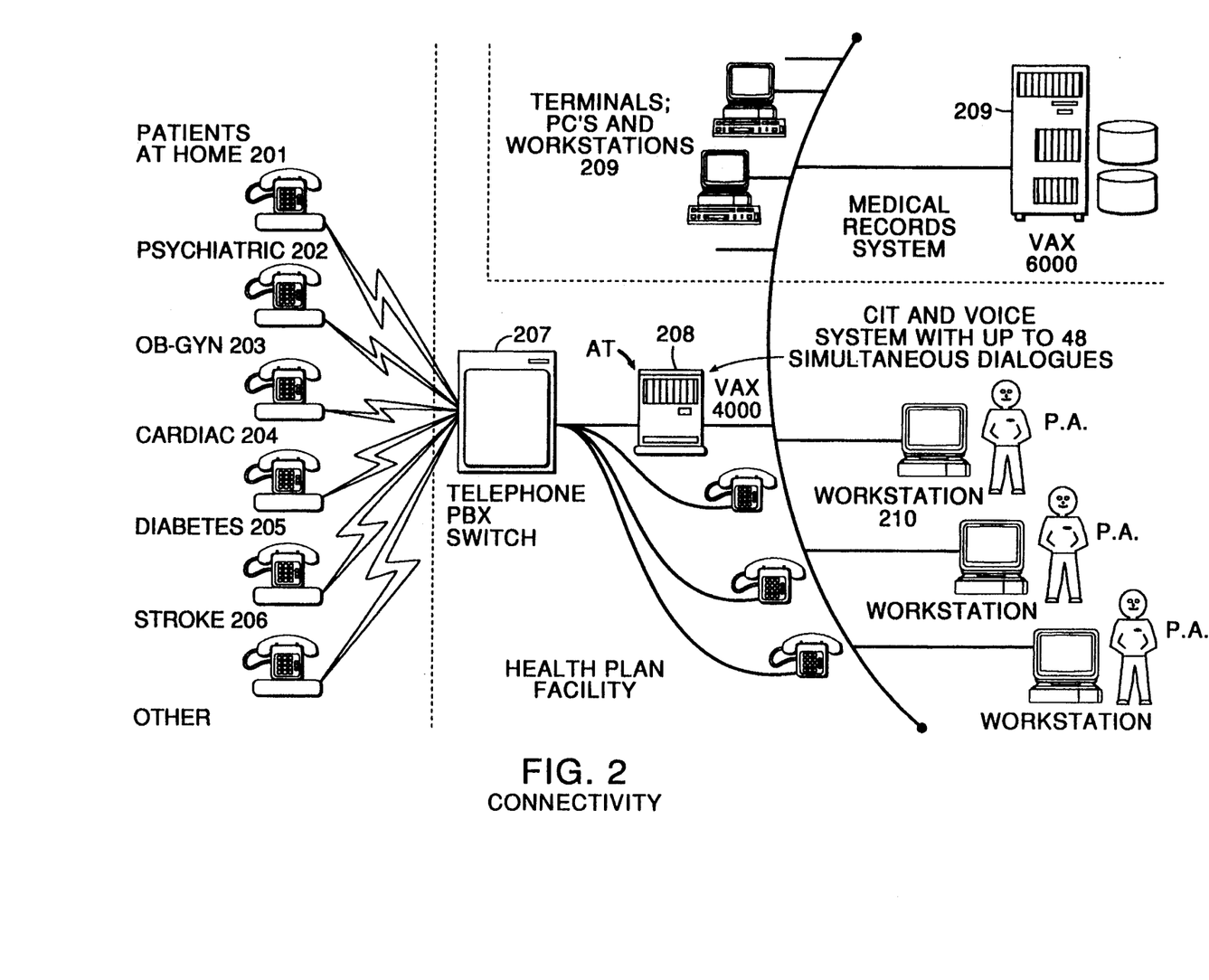
FIG. 2 illustrates pictorially a plurality of high risk patients being monitored using AI and DECvoice VAX 4000 located at a health plan facility.

An example of the voice system which can be used in the present system is illustrated as VAX 4000 in FIG. 2 wherein artificial intelligence (AI) is pictorially illustrated as combined into the VAX 4000 unit. The two elements can be provided separately.

The AI element per se could take the form of an electronic programmable read only memory (EPROM) which could be programmed considering the physician's requirements and guidelines and also taking into account the requirements of the individual patient. The EPROM assists in "PARSING" the presentations to the patient which will be triggered/selected by the patient's response to a previous question. Examples of the "Parsing" used in the system are given hereinafter in conjunction with the explanation of FIGS. 5 through 10.

Figure 3:
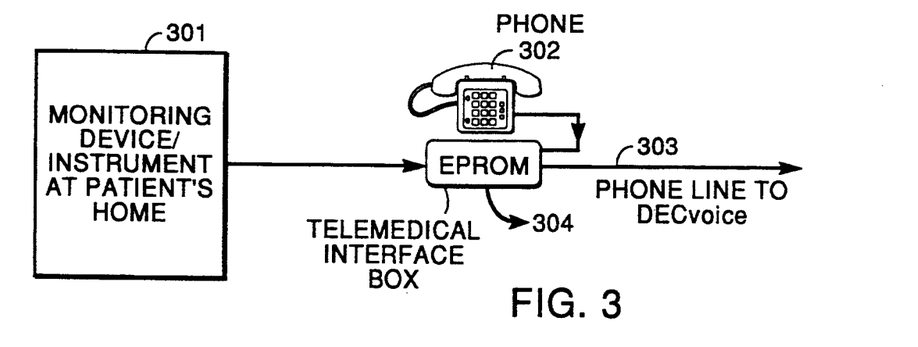
FIG. 3 illustrates a schematic representation of the connections from a monitor/instrument at a patient's home to DECvoice through a telemedical interface box.

FIG. 3 illustrates schematically an arrangement which generates signals from monitored data to be sent to DECvoice for further processing. As shown, 301 represents an instrument at patient's home. In this context, it is to be understood that the patient is a patient in distress who would need continual monitoring and consequent timely intervention by a medical practitioner.

The instrument or device 301 illustrated schematically could take the form of any of several transducers encountered in patient monitoring, e.g., blood pressure cuff, pulse monitor, uterine activity strips, glucometer, electroencephalographs, etc., it being clearly understood that the patient is not required to read the instrument or device 301. Signals so generated by 301 are connected to a telemedical interface box 304 which functions in association with a telephone 302 without a modem. Functionally, the interface box 304 validates inputs, interpolates readings and generates dual-tone matrix frequency signals which are passed on to a remotely located DECvoice unit for further processing, over line 302.

Figure 4:
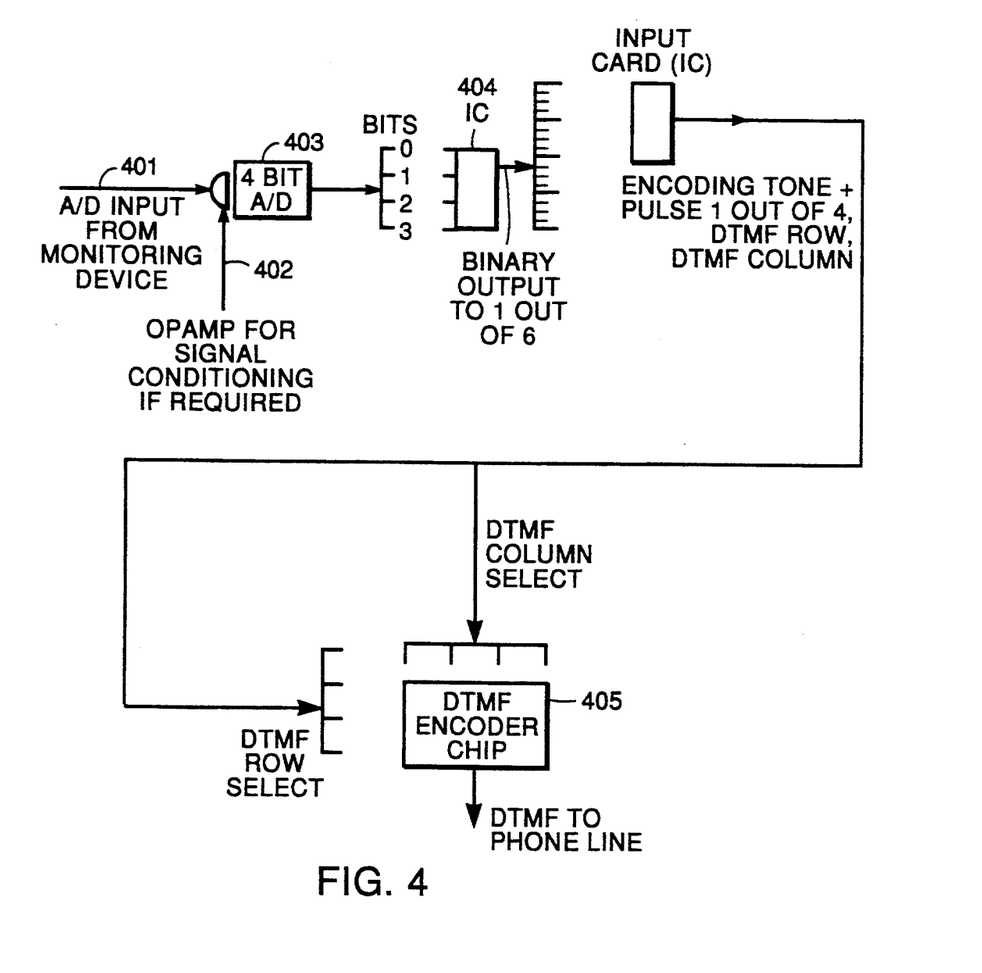
FIG. 4 schematically illustrates the circuit elements of an embodiment of a remote monitoring system using an expert system wherein AI may be built into an electronic programmable read only memory (EPROM), and using a dual-tone matrix frequency (DTMF) encoder.

FIG. 4 illustrates a high level schematic showing how monitored signals from an instrument/device at the patient's location can be conditioned encoded and converted into DTMF signals and passed on to a phone line for transmission to a remote location for being recorded, screened and analyzed on line.

A signal 401 received from an instrument, e.g., uterine activity strips, is sent through an optional operational amplifier at 402 if signal conditioning is required. Signals so conditioned are sent through a 4 bit A/D converter 403 and received by an input card 404. After performing the one out of 4 DTMF row selection and a one out of 4 DTMF column selection, the signals are processed through a DTMF encoder chip 405 which would take the form of an electronic programmable read only memory (EPROM). Examples of suitable EPROMS include Motorola MC 14410, AMI52559 and RCA CD 22951. Other EPROMS may equally be suitable.

FIG. 4 further illustrates schematically an arrangement which generates signals from monitored data to be sent to DECvoice for further processing. As shown, 401 represents an instrument at patient's home, the patient being a home-bound patient or a patient in distress who would need continual monitoring and consequent timely intervention by a medical practitioner.

The instrument or device 401 illustrated schematically corresponds to device 301 of FIG. 3 and could take the form of any of several transducers encountered in patient monitoring, e.g., blood pressure cuff, pulse monitor, uterine activity strips, glucometer, electroencephalographs, etc., it being clearly understood that the patient is not required to read the instrument or device 401. Signals so generated by 401 are connected to a telemedical interface box 404 which functions in association with a telephone 402 without a modem. Functionally, the interface box 404 validates inputs, interpolates readings and generates dual-tone matrix frequency signals which are passed on to a remotely located DECvoice unit for further processing, over line 403. Typically the DECvoice unit can simultaneously handle a plurality of lines which are limited only by the type of DECvoice unit used. A DECvoice unit capable of handling 48 lines simultaneously has been used in monitors which have already been designed. No serious limitations need exist on how many lines the DECvoice unit can accept for simultaneous handling. An example of a suitable DECvoice unit is the DECvoice 1-168 VAX System, described in the 1991 Digital Catalog entitled VAX Systems and DECsystems, Systems and Options Catalog 1991 October-December. This unit has the following capabilities:

(i) Digitized Voice
(ii) Speech Synthesis
(iii) Voice recognition and
(iv) touch tone capability whereby DTMF frequencies can be accepted, generated and detected.

In lieu of the DECvoice 1-168 unit, other commercially available units which functionally perform in a similar manner are equally acceptable.

In further reference to FIGS. 3 and 4, in addition to a first telephone line over which the patient will be presented the physician's questions and the patient will send his responses, a second telephone line in parallel with the first line is provided for transmission of signals from the monitoring device. The second telephone line includes the telemedical interface box 304 which could be a modem sized (—this is not a modem per se—) unit which houses certain hardware. Advantageously there may be jacks provided on the front of the interface box which jacks will be size keyed to various medical monitors the patient/user may have. Upon voice command (e.g., DECvoice) the user might plug in the required instrument or monitoring device (if it is not already plugged in) whereupon the reading-signal from the monitoring device is taken and DTMF encoded and transmitted to DECvoice.

Electronics inside the box might include a DTMF encoder, a 4-bit a/d converter with demultiplexer to select 1 row and 1 column from the decimal 1 of 16 (since 4 bit) D/A, and any signal conditioning circuitry. There might be a DTMF decoder, which reads a touchtone emitted by DECvoice and decodes it, causing an LED to flash above the appropriate jack, and disabling other analog inputs, so that a valid reading is taken, DTMF exchanges can only occur "for" PROM-based ID of the box (i.e. patient), or encoded data (so the user hitting touchtone keys cannot generate a valid reading of their own).

ARTIFICIAL INTELLIGENCE (AI) AND PARSING

Figure 5:
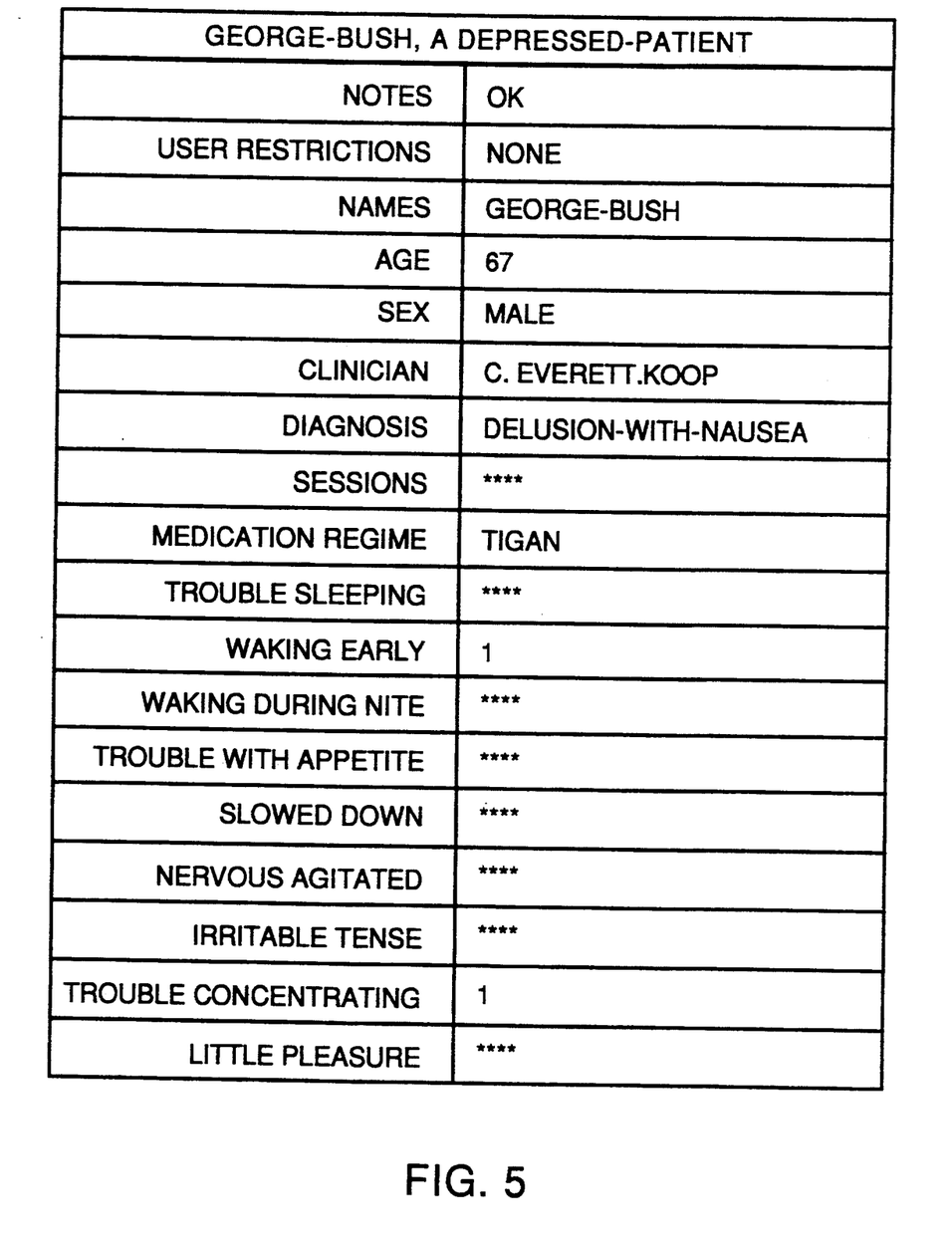
FIGS. 5 and 6 illustrate examples of patient history data and other information which would be integrated into the system in order to enable meaningful and effective "parsing" during a patient encounter.
Figure 6:
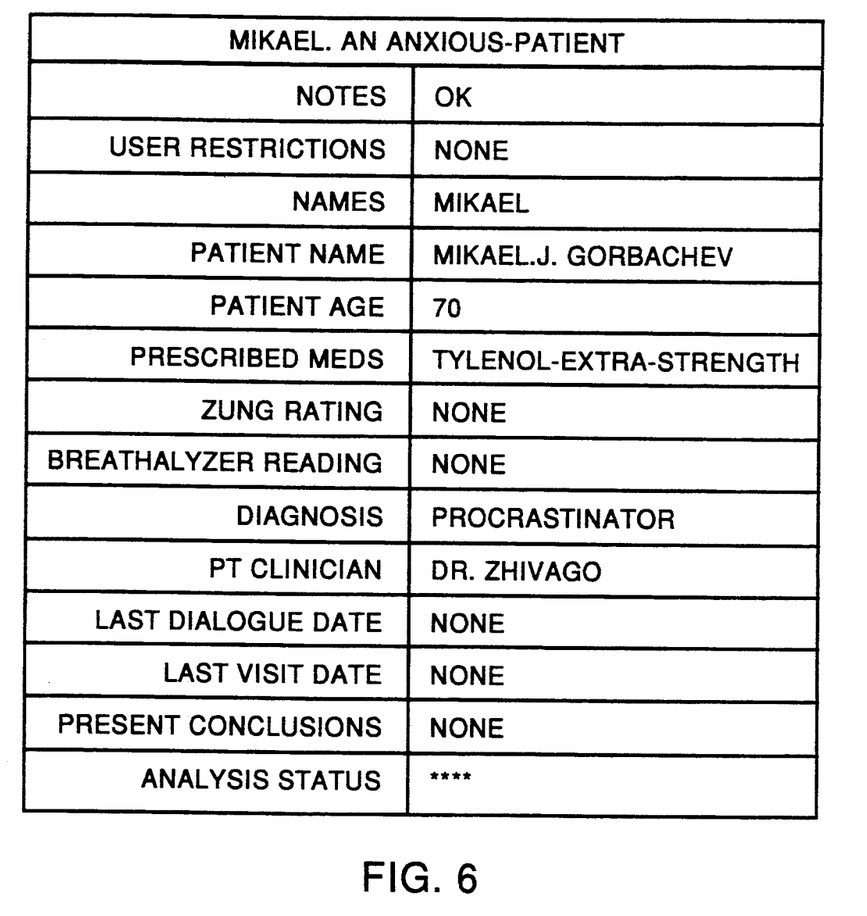
Figure 7:
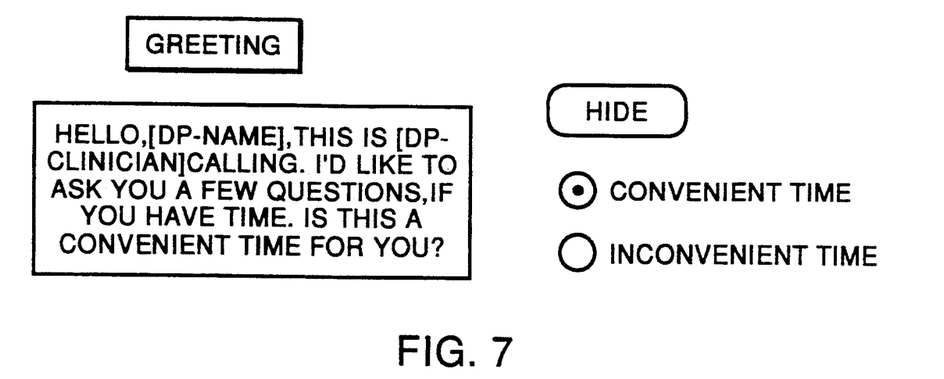
FIG. 7 illustrates a typical greeting which is parsed and tailored for encounter by a physician through a voice system, with a chosen home-bound (or depressed) patient or a high risk patient.
Figure 8:
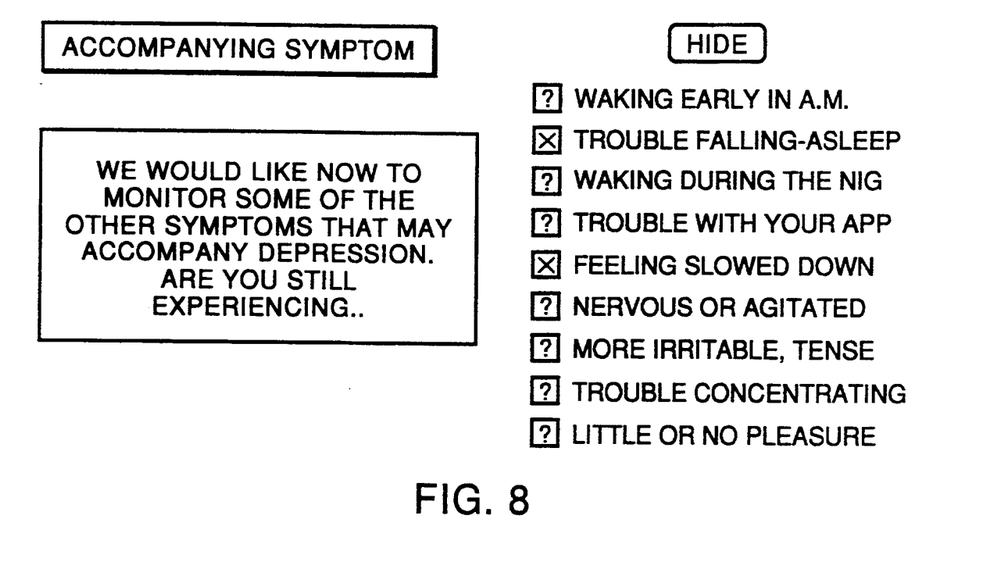
FIG. 8 illustrates examples of accompanying symptom questions which the voice system could pose to a home-bound/depressed patient.
Figure 9:
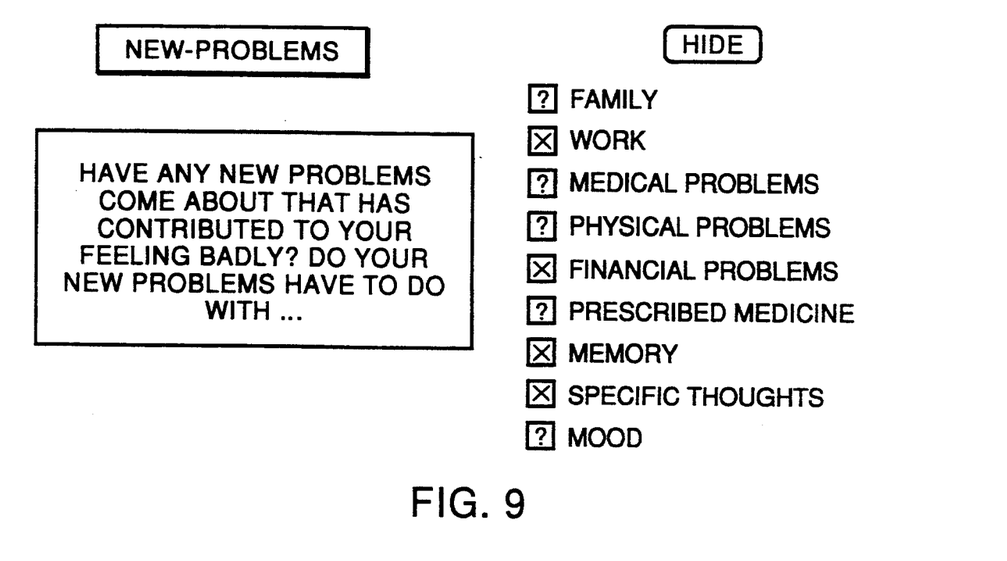
FIG. 9 illustrates a new-problem questionnaire parsed for being presented in the physician's voice to the patient.
Figure 10:
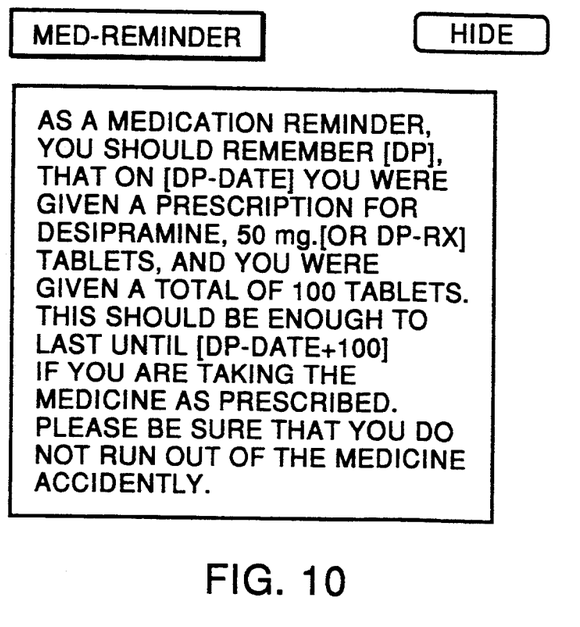
FIG. 10 illustrates a typical parsed message which will be presented to the patient in the doctor's own voice through the voice system at the conclusion of an encounter for monitoring.
Figure 11:
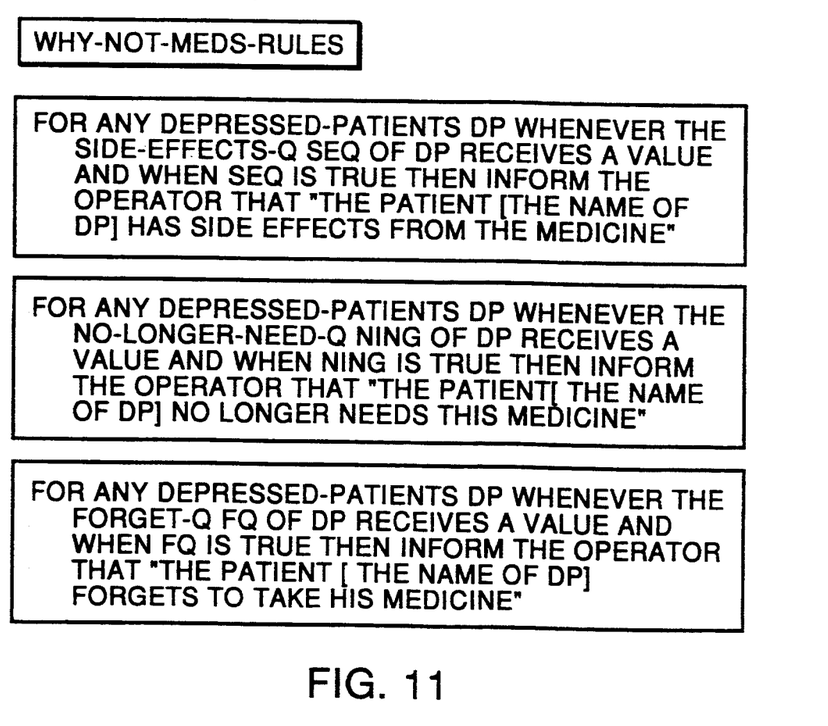
FIG. 11 is an illustration of samples of WHY-NOT-MEDS-RULES, which are self explanatory, and can be made part of the artificial intelligence content to be used in the performance of the described system.

In order that the described system should function as desired, patient information including patient data, medical history and other considerations relevant to the treatment of the patient concerned are recorded for use with the application of AI and parsing during telephone encounter with a patient to be monitored. Examples of such patient information to be recorded are illustrated in FIGS. 5 and 6. FIG. 7 shows a typical greeting which the voice system integrated into the monitoring system would present to a home-bound patient or a depressed patient represented as "dp-name". Next could follow a question which the AI program would select from a choice typically illustrated in FIG. 8. Depending on and responsive to the patient's answers, the AI program will parse, i.e., match a question as in FIG. 9 with an appropriate selection from the right hand side listing. The encounter could continue through some more questions, each time the AI program parsing to match an unfilled portion of the question from several choices, based on the AI program and the patient's response.

In this context, mention may be made of what is known as a "Turing Test" originally published in 1950 by a British computer scientist Alan F. Turing. Turing's original criterion in 1950 was that even if seven out of ten persons, conversing with a voice system for five minutes on any subject mistook the computer for a human being, then the conclusion would be that there was behavioral evidence that the computer did use logic and was thinking. The Turing test standards appear to have somewhat changed now, but the concept remains. Experiments initially conducted with the monitoring system described herein have produced very encouraging results, and a significant percentage of people who were conversing with a voice-system using AI of this invention believed that they were conversing with a human being.

COMPUTER INTEGRATED TELEPHONY (CIT)

In the example described above with reference to FIGS. 2 through 9, the processor in the CIT could be provided with means to cause a display such as for example, patient #XX has trouble sleeping or patient #YY needs attention. (See Table 1) The structural details of such displays are too well known in the art and do not form part of the generic inventive concept of this invention.

The foregoing system teaches method and apparatus using artificial intelligence and voice

TABLE 1

| MESSAGE-BOARD | |
|---|---|
| #8 7:33:33 a.m. the patient RAISA has trouble sleeping | #10 7:33:33 a.m. the patient MILLIE has trouble sleeping |
| #9 7:33:33 a.m. the patient BARB has trouble sleeping | #11 7:33:33 a.m. the patient ANDREW has trouble sleeping | technology, for remote continual monitoring of high risk patients through a monitoring device which does not have to be read by the monitored patient. The patient is greeted on the telephone in the doctor's own voice and presented questions which are selected and sequenced based on the patient's response. Based on the totality of the patient's response and the monitored reading from the monitoring device, timely intervention or change of medication or any other suitable action can be initiated by the doctor, based on the doctor's own choice and criteria. Clinically unnecessary visits are thus avoided, still preserving the integrity of patient care and not increasing the liability. While the system is described hereinbefore with examples of DECvoice, examples of depressed patients and artificial intelligence, other variations and modifications of the system with different voice systems, AI programs and different monitors are within the purview of this invention, the scope of which is defined by the appended claims.

We claim:

1. A method of remote monitoring at least one patient by using a telephone and artificial intelligence through a monitoring device which is used by the patient, without the patient having to read the monitoring device, comprising the steps of:

recording patient information including patient data, medical history and other considerations relevant to treatment of the patient concerned;

generating several questions which could be asked of the patient by an attending physician and which questions are of the physician's own choice;

creating a telephone monitoring encounter with the patient to be monitored in the doctor's own voice without the use of a modem;

using artificial intelligence (AI) for parsing said several questions to create a selection and sequence of selected questions chosen by AI from said several questions based on progressive patient response;

at the end of said sequence of selected questions, obtaining a reading signal from the monitoring device through telephone lines without a modem and by using a telephone cord splitter;

and applying physician laid down criteria for evaluating said progressive patient response and the obtained reading signal to determine any course of action necessary.

2. A method as recited in claim 1 wherein the step of obtaining a reading signal from the monitoring device comprises using dual tone matrix frequency signals.

3. A method as recited in claim 1 including the steps of using computer integrated telephony and comparing said signal from said monitoring device with physician laid down criteria, and initiating suitable intervention and action for a monitored patient.

4. A method as recited in claim 1 wherein said step of creating a telephone monitoring encounter comprises using a voice transmission means which recognizes, receives and transmits voice.

5. A system for remote monitoring of at least one patient by using telephone lines and artificial intelligence, through a monitoring device which is used by the patient, without the patient having to read the monitoring device, said system comprising:
   recorded patient information including patient data, medical history and other considerations relevant to treatment of the patient concerned;
   a plurality of physician generated questions recorded in the voice of the patient's physician, which questions could be selectively asked of the patient in the physician's voice using voice technology through telephone lines without a modem;
   a programmed read-only memory which is programmed using artificial intelligence to select applicable questions and to parse said selected questions in a sequence from said physician generated questions, based on the patient's response; and
   means without a modem for obtaining and transmitting signals from said monitoring device over telephone lines to a computer integrated telephone system, wherein by comparison of the transmitted signals with criteria predetermined by the physician, suitable intervention and action can be initiated.

6. A system as recited in claim 5 wherein said means for obtaining and transmitting signals includes a telephone cord splitter and means for encoding said obtained signals from said monitoring device into dual tone matrix frequency signals.

7. A system as recited in claim 1 including computer integrated telephony to receive said patient's response and said signals from said monitoring device.

8. A system as recited in claim 6 including a voice transmission means which has capabilities of recognizing, receiving and transmitting voice and includes memory.

9. A system as recited in claim 7 including a voice transmission means which has capabilities of recognizing, receiving and transmitting voice, and includes memory.

10. In a method of remote monitoring of at least one patient by a physician through a monitoring device which is used by the patient, without the patient having to read the monitoring device, the improvement comprising:
   recording patient information including patient data, medical history and other considerations determined by an attending physician to be relevant to treatment of a concerned patient;
   recording physician generated questions in the physician's own voice, which generated questions could be selectively asked of a patient being monitored;
   using voice-technology and creating a telephone monitoring encounter with said patient to be monitored directly through telephone lines without a modem to present to said patient selected ones of said physician generated questions;
   using artificial intelligence (AI) for parsing said several questions to create a selection of parsed questions based on progressive patient response;
   obtaining a reading signal from said monitoring device using telephone lines without a modem but using a telephone cord splitter; and
   applying physician's predetermined criteria for evaluating said progressive patient response and the obtained reading signal and concurrently determining any course of action to be taken by said physician.

11. A method as in claim 10 wherein the step of obtaining a reading signal from said monitoring device comprises using dual tone matrix frequency signals.

12. A method as in claim 10 wherein the step of using voice technology and creating a telephone monitoring encounter comprises using a voice transmission means which has capabilities of recognizing, receiving and transmitting voice, and includes memory.

* * * * *